United States Patent [19]

Webster et al.

[11] Patent Number: 5,446,218

[45] Date of Patent: Aug. 29, 1995

[54] PREPARATION OF FLUORINATED METHANES

[75] Inventors: James L. Webster, Parkersburg, W. Va.; Jan J. Lerou, Chadds Ford, Pa.

[73] Assignee: E. I. Du Pont de Nemours and Company, Wilmington, Del.

[21] Appl. No.: 213,271

[22] Filed: Mar. 15, 1994

Related U.S. Application Data

[63] Continuation-in-part of Ser. No. 51,917, Apr. 26, 1993, abandoned.

[51] Int. Cl.$^6$ ............................................. C07C 17/08
[52] U.S. Cl. ..................... 570/169; 570/166; 570/167; 570/168
[58] Field of Search ................ 570/169, 166, 167, 168

[56] References Cited

U.S. PATENT DOCUMENTS 3,442,962  5/1969  Vecchio et al. .

FOREIGN PATENT DOCUMENTS 1017152  1/1966  United Kingdom .

*Primary Examiner*—Alan Siegel
*Attorney, Agent, or Firm*—Edwin Tocker

[57] ABSTRACT

A single step, vapor phase process for the chlorofluorination of methane forms trifluoromethane and/or tetrafluoromethane in high yield. A $Cr_2O_3$ catalyst is preferred.

18 Claims, 1 Drawing Sheet

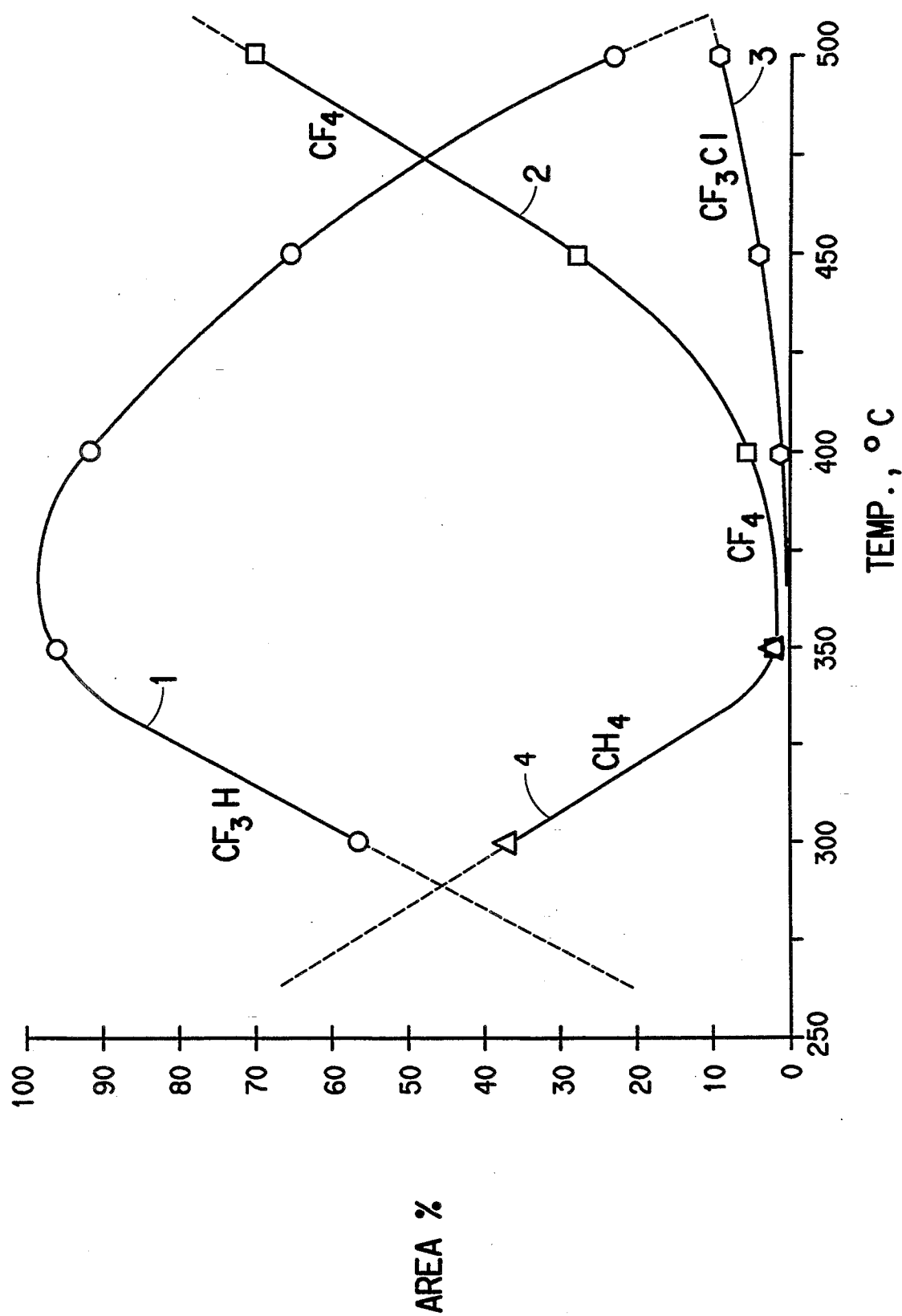

PREPARATION OF FLUORINATED METHANES

FIELD OF THE INVENTION

This application is a continuation-in-part of application Ser. No. 08/051,917, filed Apr. 26, 1993, now abandoned.

This invention relates to the preparation of trifluoromethane ($CF_3H$) and tetrafluoromethane ($CF_4$).

BACKGROUND OF THE INVENTION $CF_3H$ is useful as a precursor for the formation of tetrafluoroethylene, which can be polymerized to polytetrafluoroethylene. $CF_4$ is useful for a plasma activating agent in the semiconductor industry. Heretofore, these compounds have been made in high yields as desired reaction products in two process steps: first a chlorinated intermediate is formed, e.g. starting from methane, followed by fluorination of this intermediate. Thus, $CCl_4$ has been reacted with HF to obtain $CF_4$. Example 4 of U.S. Pat. No. 3,258,500 discloses the reaction of HF with $CCl_3H$ to make $CF_3H$; this is the second process step. Synthesis of the $CCl_3H$ starting material is the first process step. U.S. Pat. No. 3,652,692 discloses reacting $CH_4$ with $Cl_2$ in a first step to form chloromethanes, followed by reacting the chloromethanes with HF.

Chlorofluoromethanes have been made in one-step by simultaneously reacting $CH_4$ with $Cl_2$ and HF. See U.S. Pat. Nos. 2,407,129, 3,294,852, and 3,442,962.

British Patent 1,017,152, discloses the reaction of $CH_4$ with $Cl_2$, and HF in the presence of a large proportion of halogenated hydrocarbon. The major reaction products disclosed are $CF_2Cl_2$ and $CFCl_3$. Example 10 also discloses $CF_3H$ as a small amount of reaction product and $CCl_4$ as a major reaction product when large proportions of $CCl_3H$ and $CHFCl_2$ precursors to $CF_3H$ were present in the halogenated hydrocarbon feed to the reaction. U.S. Pat. No. 3,258,500 discloses $CCl_3H$ to be a precursor for $CF_3H$ and U.S. Pat. No. 3,652,692 discloses the presence of $CHFCl_2$ in the reaction of chloromethane with HF to form $CF_3H$ in the second step of the process.

SUMMARY OF THE INVENTION

The present invention involves the discovery of a one-step process, starting with methane ($CH_4$), for making $CF_3H$ and/or $CF_4$ in high yields. The process may be described with reference to the process disclosed in British Patent 1,017,152 as follows: In the process of preparing halogenated methane by reacting $CH_4$ simultaneously with $Cl_2$ and HF in the presence of halogenated hydrocarbon as essential compounds present during the reaction and a halogenation catalyst at a temperature between 200° C. and 700° C. and with a contact time of less than 30 sec., wherein said halogenated methane is primarily $CF_2Cl_2$ and $CFCl_3$, except that when said halogenated hydrocarbon contains a substantial amount of $CHCl_3$ and $CHClF_2$, then a substantial amount of $CCl_4$ and a small amount of $CF_3H$ is formed, the improvement comprising carrying out said reacting wherein (a) the molar ratio of $CH_4/Cl_2/HF$ is at least 1/3/3,
(b) the $CH_4$, $Cl_2$ and HF are the essential compounds present during the reaction, and
(c) the halogenation catalyst and reaction conditions produce a substantial amount of $CF_3H$ and/or $CF_4$ reaction products.

The process may also be described as comprising contacting and reacting $CH_4$ simultaneously with $Cl_2$ and HF as the essential compounds present during said reacting, all in the gaseous state, under such conditions of temperature, presence of thermally stable chlorofluorination catalyst, catalyst contact time, and ratio of reactants to obtain as a result thereof a substantial amount of at least one reaction product selected from the group consisting of $CF_3H$, $CF_4$, and the combination thereof, preferably at least 50 mol % thereof.

Unexpectedly, although $Cl_2$ is a reactant, the major reaction products of the process of the present invention are chlorine-free. Surprisingly, high yields of $CF_3H$ can be obtained, i.e., one of the H atoms from $CH_4$ remains unreacted even though highly reactive $Cl_2$ is present during the conversion of $CH_4$ to $CF_3H$.

The advantage of the present one-step process over the prior two-step process, in addition to simplicity and economy of operation, includes the fact that chlorocarbon compounds need not be major reaction products or feed materials which are isolated, handled, or stored as intermediates.

BRIEF DESCRIPTION OF THE DRAWING

The drawing is a plot of gas chromatography analysis results of the reactor effluent of the experiment described in Example 3. Curve 1 represents the proportion of $CF_3H$. Curve 2 represents the proportion of $CF_4$. Curve 3 represents the proportion of $CF_3Cl$ by-product. Curve 4 represents the proportion of $CH_4$. Curve 4 ends at the data point at 350° C. which is coincidentally superimposed on the data point for the beginning of Curve 2. The proportion of each compound is presented as the normalized area (area %) of the gas chromatography peak for each compound.

DETAILED DESCRIPTION OF INVENTION

The process of the present invention can be carried out in equipment conventionally used for gas phase chlorofluorination. Preferably the reactor is a tubular reactor having a zone which is packed with thermally stable chlorofluorination catalyst to form a catalyst bed through which the gaseous reactants pass. The halogenation conditions are selected to produce the substantial amount; e.g., at least 25 mol %, or higher yield, of $CF_3H$ and/or $CF_4$.

With respect to reaction conditions, the reaction will generally be carried out within the range of about 250° to 600° C., with the particular temperature selected to produce the amount of $CF_3H$ and $CF_4$ desired in the reactor effluent in accordance with the following equations:

(1) $CH_4 + 3Cl_2 + 3HF \rightarrow CF_3H + 6HCl$
(2) $CH_4 + 4Cl_2 + 4HF \rightarrow CF_4 + 8HCl$
(3) combination of (1) and (2).

The results of the particular reaction conditions from which the drawing was produced show a rapid increase in production of $CF_3$. It from 300° to 360° C. and decrease in production of $CF_3H$ and almost concomitant increase in production of $CF_4$ as the temperature increases above 360° C. For these particular reaction conditions, the highest production of $CF_3H$ occurs at about 360° C. For other reaction conditions, the highest production will occur at different temperatures. It has been found that the preferred temperature range for producing $CF_3H$ is from 300° to 425° C.

Process conditions, e.g. catalyst contact time within this temperature range, can be selected so as to produce at least 50 mol % $CF_3H$ in the reactor effluent. The highest productions of $CF_3H$, e.g. at least 70 mol % or at least 90 mol % and even at least 95 mol %, occur in increasingly narrow temperature ranges. The composition of the reactor effluent described herein, unless otherwise indicated, refers to analysis of the effluent after removal of HCl reaction product and unreacted $Cl_2$ and HF from the effluent. More preferred temperature ranges for $CF_3H$ production will be from 325° to 400° C. and 350° to 375° C. The reaction conditions are also selected to give a high conversion of $CH_4$ to desired product, e.g. a conversion of at least 80%, preferably at least 90%, and more preferably at least 95%, with respect to the amount of $CH_4$ fed to the reactor.

For the production of 50 mol % $CF_4$ or higher in the reactor effluent, the reaction temperature is about 450° to 550° C., with the highest temperature being selected so as to produce a substantial production of $CF_4$ with minimized production of chlorotrifluoromethane. For the particular embodiment shown in the drawing, operation at about 450° C. reaction temperature produces about 94 mol % of $CF_3H$ and $CF_4$ combined.

The temperature of reaction described herein refers to the temperature measured midway along the length of the reaction zone (catalyst bed) in the tubular reactor unless otherwise indicated. This temperature arises mainly from the heating of the gaseous reactants fed to the reaction zone plus the heat of reaction occurring therein.

The simultaneous reaction of the $Cl_2$ and the HF with $CH_4$ refers to the fact that $Cl_2$ and HF are present with the $CH_4$ in the reaction zone at the same time. Thus the reaction converting $CH_4$ to $CF_3H$ and/or $CF_4$ can be called a one-step reaction. The reaction time, which is the time that the reactants are in contact with the catalyst, i.e., catalyst contact time, at the reaction temperature and pressure is generally very short, ranging from a fraction of a second, e.g. 0.1 sec up to 10 seconds and typically 0.5 to 5 seconds, although the catalyst contact time can often be less than 2 or 3 seconds. At low reaction temperatures; e.g., 250° to 300° C., longer catalyst contact times can increase the amount of $CF_3H$ produced.

The catalyst is selected to be thermally stable at the reaction temperature (in the sense of remaining as a solid and being substantially non-volatile, i.e., the catalyst does not disappear), to promote the chlorofluorination of $CH_4$, and to produce the desired result of chlorine-free fluorinated products described hereinbefore. A variety of catalysts are effective in this regard. For example, the catalyst installed in the reactor may be metal oxide or halide wherein the metal is from Groups IIA, IIB, notably Zn, IIIB, notably B and Al, VIA, notabley Cr, or VIIIA, notably Fe, Co, and Ni of the Periodic Table (IUPAC 1970 system). Preferred catalysts are gattuna $Al_2O_3$, $Cr_2O_3$ and $CoCl_2$. It will be recognized that the installed catalyst; i.e., present at the start of the reaction, may be modified by reaction with $Cl_2$ and/or HF present during the reaction. In the light of the present teaching of the ability to start with $CH_4$ and end up with chlorine-free fluorinated reaction products, one skilled in the art will be able to find additional chlorofluorination catalysts to produce this result. The catalyst is preferably activated prior to commencement of the reaction and may be regenerated (reactivated) as catalytic activity diminishes.

The process is preferably carried out with ratio of reactants $CH_4/Cl_2/HF$ of at least 1/3/3 to make $CF_3H$ and at least 1/4/4 to make $CF_4$. Thus, for each H atom to be reacted from the C-containing sources there should be at least one F and at least 2 Cl atoms available. The excess chlorine would be expected to replace all of the H atoms of the methanes, but surprisingly, the present invention discovered this does not happen, making it possible to obtain new $CF_3H$ and/or $CF_4$ from $CH_4$ in one step, without production of appreciable amounts of chlorine-containing intermediate products. Thus, for high amounts of $CF_3H$ formed in the reaction; e.g., at least about 90 mol % present in the reactor effluent, the amount of chlorocarbon (chlorine-containing carbon compound) formed is quite small; i.e., less than about 10 mol %, preferably less than about 5 mol %. The same can be true for lesser amounts of $CF_3H$ formed in the reaction when the major effluent compound other than $CF_3H$ and $CF_4$ is unreacted $CH_4$. Independently, even greater excess molar amounts of HF and $Cl_2$ reactants are preferred; e.g., 1/4/6 and even greater excess, e.g. 1/7/10. Thus, the preferred ratio of $CH_4/Cl_2$ is $\frac{1}{4}$ to 1/7 and of $CH_4/HF$ is 1/6 to 1/10. Molar ratios of 1/9/12 and as high as 1/10/20 can also be used. Unconverted $CH_4$ and unreacted HF and $Cl_2$ and by-products can be recycled to the reaction zone for participation in the reaction and moderation of the heat of reaction. The presence of recycled excess unreacted reactant and any by-product in the reaction zone helps moderate the heat of the reaction, but the presence of these compounds are not essential to the production of high yields of $CF_3H$ and/or $CF_4$. The $CH_4$, $Cl_2$, and HF are the essential compounds (reactants) needed in the reaction to produce this result.

The desired reaction products $CF_3H$ and $CF_4$ are recovered from the reaction product gaseous stream by conventional means.

Upon becoming informed of the present invention, one skilled in the art will recognize many variations that can be made in the invention described herein. For example, instead of using a tubular reactor, other forms of reactors used for gas phase reactions can be used to practice the present invention; e.g., a fluid bed reactor. The experiments described in the Examples herein operate the reactor at atmospheric pressure for convenience; the reactor used to practice the present invention can just as well be practiced at reduced pressure or at elevated pressure; e.g., 250 psig (1723 KPa) so as to provide the driving force for separation of the reactor effluent into desired components.

Examples of the process of the invention are as follows.

EXAMPLE 1

Catalyst Preparation

Preparation of $Cr_2O_3$ catalyst in the form of pellets is disclosed in U.S. Pat. No. 5,036,036.

Process

A $\frac{1}{2}$ inch (1.3 cm) diameter tube, 16 inches (40.6 cm) long, made from "Inconel" 600 ("Inconel" is a registered trademark of The International Nickel Company) was filled with 40 g of $Cr_2O_3$ catalyst made according to the procedure above. Importantly, the catalyst filled the tube so that preheating was done primarily on the surface of the catalyst and not by the reactor walls. The catalyst pellets had been crushed and sized by screening through a 7 mesh screen onto a 10 mesh screen. A tee was place on the exit end of the packed reactor tube so a thermowell with a thermocouple could be placed close to the midpoint of the catalyst bed in the reactor. The reactor was placed in a standard, single control, twelve inch (30.5 cm) long split shell furnace. A mass flowmeter was used to measure the needle valve controlled flow of anhydrous hydrogen fluoride from a small cylinder set in a bucket of 40° C. water. Flows of methane, chlorine, and nitrogen were all controlled by small needle valves and measured by glass tube rotometers. Should there have been a plug in the reactor, the entire feed system had the capability to be relieved through a dip tube, 6 inches (15.2 cm) below the surface of a mercury reservoir. The flow from the reactor system emptied into a small knockout pot, which was used to keep any scrubbing liquids from being drawn back into the reactor when the feeds were stopped and the reactor was cooled. In some tests, a small flow of nitrogen was used as an inert sweep gas through the reactor. The product gases from the knockout pot (effluent from the reaction) were scrubbed through a 20% KOH solution and then through a water scrubber to remove the HCl and remaining chlorine and HF. The gases were then dried by passing through a bed of calcium sulfate particles. Sampling of the product stream was usually done after the drying step, but could be done at the exit of the reactor or after the scrubbing steps to verify that the scrubbing was not affecting the results. The samples were routinely analyzed on a gas chromatograph with a thermal conductivity detector and the results presented as area percents, which is a close approximation of the mol % of each product in the reactor effluent after removal of HCl, and unreacted $Cl_2$ and HF. The gas chromatographic column used was purchased from Supelco, Inc. and was a 0.125 inch (3.2 mm) diameter stainless steel column 8 ft (3.66 m) long containing 1% Supelco's SP-1000 on 60/80 mesh Carbopack B. This column separated all of the various components except for the small proportion of $CF_4$ that might have been present accompanying unreacted $CH_4$.

Start-up of the reactor system was accomplished by heating the reactor to about 250° C. with nitrogen flowing through the system. Then a mixture of nitrogen and HF was passed through the system, at some temperature at or above the desired reaction temperature for one hour to help activate the catalyst. With the catalyst so activated and while still under the HF flow, but with nitrogen flow discontinued, the reactor was cooled down to the desired reaction temperature and the other process flows of $CH_4$ and $Cl_2$ were started. For the data and results shown in Table 1, the reactor had been heated under HF and $N_2$ flow to 479° C. before being cooled down to reaction temperature. In Table 1 (and Tables 2 and 3) the ratio values are the molar ratios of $CH_4/Cl_2/HF$ in the feed. The total amount of reactant feed is shown in g-mol per hour and if any nitrogen was used with the feed, it is shown separately. The catalyst contact times listed are based on the assumption that the middle 20 cm of the reactor tube (1.09 cm inside diameter) were at or near the listed reaction conditions and that the reactor volume is further reduced by a 0.5 factor because of the catalyst volume. The total elapsed time that a given charge of catalyst had been operating with a reactive feed is shown as total elapsed time in hours. The retention time in minutes for each component as it elutes on the gas chromatograph is shown, as is the product identification. All components, not shown otherwise, are totaled in the product column opposite the miscellaneous label. The unconverted $CH_4$ reported in Table 1 can contain a small proportion of $CF_4$.

TABLE 1

| CONDITIONS AND RESULTS FOR EXAMPLE 1 | | | |
|---|---|---|---|
| | A | B | C |
| $CH_4/Cl_2/HF$ | 1/5.0/7.4 | 1/5.0/7.3 | 1/5.2/7.3 |
| Rate (g-mol/hr) | 1.07 | 1.06 | 1.037 |
| Contact Time (sec) | 0.63 | 0.66 | 0.68 |
| $N_2$ (g-mol/hr) | 0.04 | — | — |
| Elapsed Time (hr) | 1.5 | 3.25 | 5.25 |
| Temp. (°C.) | 378 | 375 | 376 |
| Retention Time (min) | Product Ident. | Area % | Area % | Area % |
| .62/.65 | $CH_4$ | 4.9 | 3.7 | 3.7 |
| 0.77 | $CF_3H$ | 93.3 | 94.9 | 95.1 |
| 1.18 | $CF_3Cl$ | 0.9 | 0.7 | 0.7 |
| | Misc. | 0.9 | 0.7 | 0.5 |

EXAMPLE 2

The equipment and procedure in this example are the same as in Example 1 except that a new charge of the chromium oxide catalyst was used and the system was brought on line by purging with nitrogen up to 250° C. and then adding HF until a temperature of 371° C. was reached and the process feeds started. Results are summarized in the accompanying Table 2.

More complete analysis of the tetrafluoromethane-/methane/carbon tetrafluoride chromatograph peak of run A showed that it was 99.9% methane and 0.1% tetrafluoromethane. For run C, the 3% peak in the reactor effluent was about a 50/50 mol mixture of methane and tetrafluoromethane. The sample for run B had a contact time close to 1.5 seconds, showing that longer contact time gave a slightly higher conversion of methane to $CF_3H$. A reduction in chlorine for run D and a reduction in HF for run E both give less favorable results. Thus, this Example shows the effect of the variation of such reaction conditions as catalyst contact time and ratio of the reactants in the feed to the reactor.

The results of this Example also show that for these particular reaction conditions that the increase in reaction temperature from 277° C. to the range 370° to 374° greatly increases the conversion of $CH_4$ and produces very high yields of $CF_3H$.

TABLE 2

| CONDITIONS AND RESULTS FOR EXAMPLE 2 | | | | | |
|---|---|---|---|---|---|
| | A | B | C | D | E |
| $CH_4/Cl_2/HF$ | 1/5.1/7.4 | 1/4.9/6.5 | 1/4.8/7.3 | 1/3.9/6.2 | 1/8.0/3.9 |
| Rate (g-mol/hr) | 1.037 | 0.457 | 1.007 | 1.119 | 1.03 |
| Contact Time (sec) | 0.77 | 1.47 | 0.70 | 0.63 | 0.68 |
| $N_2$ (g-mol/hr) | 0.04 | 0.02 | — | — | — |
| Elapsed Time (hr) | 2.75 | 11.75 | 22.75 | 26.25 | 38.75 |
| Temp. (°C.) | 277 | 374 | 370 | 373 | 372 |

TABLE 2-continued

| CONDITIONS AND RESULTS FOR EXAMPLE 2 | | | | | | |
|---|---|---|---|---|---|---|
| Retention Time (min) | Product Ident. | Area % | Area % | Area % | Area % | Area % |
| .62/.65 | $CH_4$ | 57.7 | 2.0 | 3.0 | 11.0 | 4.2 |
| 0.77 | $CF_3H$ | 28.7 | 97.2 | 95.7 | 84.3 | 93.4 |
| 1.18 | $CF_3Cl$ | 0.1 | 0.4 | 0.3 | 1.3 | 0.8 |
| | Misc. | 13.5 | 0.4 | 1.0 | 3.4 | 1.6 |

EXAMPLE 3

The equipment and procedures in this example are the same as those used in Example 1, except after preheating with nitrogen to 250° C., a flow of 35 to 40 cm³/min. of HF was used as the temperature of the reactor was taken to 450° C. and held there for two hours. The reactor temperature was then reduced to the desired operating temperature before the methane and chlorine flows were started. For this particular example, all of the analyses were performed on a gas chromatograph with a column similar to that described in Example 1 but 2.5 times longer thus achieving the complete separation of the methane peak from the tetrafluoromethane peak. Data obtained are recorded in Table 3. A plot of gas chromatograph results versus temperature gives the graph shown in the drawing. The graph displays the relative amounts of unreacted $CH_4$ and $CF_3H$, $CF_4$ and $CF_3Cl$ formed as temperature is varied.

These results show that as the reaction temperature increases from 300° C. the yield of $CF_3H$ increases remarkably, and at temperatures of 360° C. and higher, the yield of $CF_3H$ progressively declines while the yield of $CF_4$ increases. Even at 500° C., the combined yield of desired $CF_3H$ and $CF_4$ reaction product is about 91%.

TABLE 3

| CONDITIONS AND RESULTS FOR EXAMPLE 3 | | | | | |
|---|---|---|---|---|---|
| | A | B | C | D | E |
| $CH_4/Cl_2/HF$ | 1/5.0/6.9 | 1/5.0/7.0 | 1/4.8/6.8 | 1/5.0/7.0 | 1/4.8/6.6 |
| Rate (g-mol/hr) | 0.694 | 0.704 | 0.706 | 0.704 | 0.696 |
| Contact Time (sec) | 1.01 | 0.80 | 1.08 | 0.86 | 0.93 |
| $N_2$ (g-mol/hr) | 0.03 | 0.03 | 0.03 | 0.03 | 0.03 |
| Elapsed Time (hr) | 2.75 | 3.75 | 6.0 | 8.0 | 10.0 |
| Temp. (°C.) | 348 | 500 | 300 | 449 | 401 |

| Retention Time (min) | Product Ident. | Area % | Area % | Area % | Area % | Area % |
|---|---|---|---|---|---|---|
| 2.38 | $CH_4$ | 1.3 | 0.1 | 37.0 | 0.1 | 0.1 |
| 2.56 | $CF_4$ | 0.9 | 68.6 | 0.0 | 28.8 | 5.9 |
| 3.09 | $CF_3H$ | 96.1 | 22.2 | 56.0 | 65.3 | 90.5 |
| 5.47 | $CF_3Cl$ | 0.6 | 8.3 | 0.1 | 3.6 | 1.6 |
| | Misc. | 1.1 | 0.8 | 6.9 | 2.2 | 1.9 |

EXAMPLE 4

In this example, the chlorofluorination catalyst was 3.5 g of the $Cr_2O_3$ catalyst prepared as in Example 1. This catalyst bed was located in the middle of a 0.5 inch (1.3 cm) diameter tube of Inconel 600, heated by a 12 inch (30.5 cm) long Lindberg split shell furnace. $CH_4$, $Cl_2$, and HF and were metered by thermal mass flowmeters. The catalyst was activated with heated HF. The flow rates in standard cm³/min were 5 for $CH_4$, 25 for $Cl_2$, and 35 for HF, thus giving the molar ratio $CH_4/Cl_2/HF$ equal to 1/5/7. The reactor effluent (after removal of HCl and unreacted $Cl_2$ and HF) was analyzed by an on-line gas chromatograph with a 0.125 inch (0.3 cm) diameter column 20 ft (6.1 m) long containing perfluorinated polyether (KRYTOX® grade 143HMW, DuPont Co.) on an inert support, and with a helium carrier gas flow of 30 standard cm³/min. $CF_4$ and $CH_4$ are listed together as $CH_4$ in Table 4 which expresses, in area %, the constituents identified in the reactor effluent stream for various reaction temperatures. The difference between 100 and the sum of the figures for the named components at a given reaction temperature is the total of other miscellaneous components in the reactor effluent at that condition. The values in the HOS column are hours on stream (elapsed time) at the listed reaction conditions. The reaction temperatures were employed in the sequence shown from top to bottom. These results show the highest yields of $CF_3H$ occurring at and between reaction temperatures of 325° to 400° C.

TABLE 4

| CONDITIONS AND RESULTS FOR EXAMPLE 4 | | | | | | |
|---|---|---|---|---|---|---|
| T(°C.) | Contact Time (sec) | $CH_4$ (%) | $CF_3H$ (%) | $CF_3Cl$ (%) | Misc. (%) | HOS (hr) |
| 300 | 1.10 | 40.0 | 36.3 | — | 23.7 | 16 |
| 400 | 0.94 | — | 92.5 | 5.7 | 1.8 | 31 |
| 350 | 1.01 | — | 97.9 | 1.2 | 0.9 | 20 |
| 300 | 1.10 | 40.5 | 32.9 | — | 26.6 | 16 |
| 325 | 1.05 | 1.6 | 97.1 | 0.3 | 1.0 | 16 |
| 275 | 1.15 | 81.7 | 5.7 | — | 12.6 | 8 |
| 250 | 1.20 | 90.4 | — | — | 9.6 | 8 |

EXAMPLE 5

Equipment used was similar to that described in Example 4, with the following exceptions. The catalyst was placed at the bottom of a vertical 0.75 inch (1.9 cm) diameter and 9 inch (22.9 cm) long tube of Inconel 600, heated in a sand bath. With this heating system, temperature increases of 25° C. were accomplished in about 10 min, increases of 50° C. in about 15 min. The inlet for feed gases was at the top and the outlet was at the bottom of the reactor tube. The on-line GC was coupled to a mass spectrometer (Hewlett-Packard Series 5970) and was calibrated with known compounds to give reactor effluent constituents in mol %.

The catalyst was 19.1 g (30 cm$^3$) of commercially available gamma alumina, activated as follows. The bath was heated to 175° C. while N$_2$ was passed through the reactor at a rate of 50 cm$^3$/min to remove traces of water. An equal flow of HF was added to the N$_2$ and the mixed stream flow was continued until exothermic activity ceased. While maintaining the same total flow, HF and N$_2$ flows were adjusted to the molar ratio HF/N$_2$=4/1. The temperature was gradually raised to 400° C. and maintained there for about 30 min during which N$_2$ flow was reduced by half. The temperature was then reduced to the initial test value, reactant flows were started, and N$_2$ flow was discontinued.

For this example, the feed flow rates were in the molar ratio CH$_4$/Cl$_2$/HF=1/5/7. Total feed flow rate was set to give a room temperature contact time of 5 sec, calculated as the volume of the reactor in cubic centimeters (cc) occupied by the catalyst, divided by the feed flow in cc/sec at room temperature. The actual catalyst contact time would be shorter because of the volume expansion of the gases at reaction temperature. For example, from Table 5, the room temperature contact time of 5 sec. is in fact a catalyst contact time of about 2.2 sec. at 400° C. A summary of results is shown in Table 5. HCl and unreacted Cl$_2$ and HF were removed from the reactor effluent prior to analysis of the reaction product stream. The time shown is cumulative time during the sequence of tests, starting from an idling temperature of 120° C.

These results show that at 400° C., the highest proportion of CF$_3$H was obtained, the proportion (mol %) at that temperature improving from the 27th to the 28th hour of operation and tailing off at the 29th hour of operation. This tailing off suggests the catalyst was deteriorating and required regeneration or replacement. At the highest production of CF$_3$H of 82.1 mol %, the amount of CF$_3$Cl was 10.7 mol % and the remaining reaction products (Other) totaled more than eight such products in concentrations ranging from 0.1 to 1.7 mol % per product.

TABLE 5

| | | RESULTS FOR EXAMPLE 5 | | | |
|---|---|---|---|---|---|
| Elapsed Time (hr) | T (°C.) | Effluent Stream Constituents (mol %) | | | |
| | | CH$_4$ | CF$_3$H | CF$_3$Cl | Other |
| 1 | 150 | 92.3 | 0.0 | 0.0 | 7.7 |
| 5 | 250 | 90.1 | 0.0 | 0.0 | 9.9 |
| 14 | 300 | 69.2 | 1.9 | 0.0 | 28.9 |
| 21 | 300 | 46.0 | 4.1 | 0.0 | 49.9 |
| 22 | 350 | 27.5 | 26.8 | 0.1 | 45.6 |
| 24 | 350 | 26.6 | 13.5 | 0.4 | 59.5 |
| 26 | 350 | 24.1 | 15.2 | 0.5 | 60.2 |
| 27 | 400 | 0.1 | 60.4 | 33.2 | 6.3 |
| 28 | 400 | 0.3 | 82.1 | 10.7 | 6.9 |
| 29 | 400 | 0.3 | 34.3 | 47.6 | 17.8 |
| 30 | 375 | 7.6 | 49.6 | 0.6 | 42.2 |

EXAMPLE 6

The same equipment and procedures were used as in Example 5, except that the initial catalyst charge was 19.5 g (15 cm$^3$) of Cr$_2$O$_3$ produced by the method outlined under Example 1. Results are shown in Table 6.

These results show the highest yields of CF$_3$H beginning at a temperature between 300° and 325° C. and continuing in the range of 325° to 350° C. As for other reaction products formed within the 325° to 350° C. temperature range, other than 0.1 mol % CF$_3$Cl, they comprised three such products, the largest amount of which was 1.9 mol % CCl$_4$.

TABLE 6

| | | RESULTS FOR EXAMPLE 6 | | | |
|---|---|---|---|---|---|
| Elapsed Time (hr) | T (°C.) | Effluent Stream Constituents (mol %) | | | |
| | | CH$_4$ | CF$_3$H | CF$_3$Cl | Other |
| 2 | 200 | 92.4 | 0.4 | 0.0 | 7.2 |
| 5 | 250 | 79.7 | 0.1 | 0.0 | 20.2 |
| 6 | 250 | 78.5 | 0.1 | 0.0 | 21.4 |
| 7 | 275 | 60.8 | 5.9 | 0.1 | 33.2 |
| 10 | 275 | 55.9 | 7.8 | 0.1 | 36.2 |
| 11 | 300 | 13.3 | 74.6 | 0.1 | 12.0 |
| 15 | 300 | 12.8 | 72.3 | 0.1 | 14.8 |
| 16 | 325 | 1.3 | 96.9 | 0.1 | 1.7 |
| 20 | 325 | 1.3 | 96.8 | 0.1 | 1.8 |
| 21 | 350 | 0.1 | 97.5 | 0.1 | 2.3 |

EXAMPLE 7

The same equipment and procedures were used as in Example 5, except that the initial catalyst charge was 17.9 g (15 cm$^3$) of a commercial sample of Cr$_2$O$_3$ with surface area greater than 100 m$^2$/g as measured by N$_2$ BET. Results are shown in Table 7.

These results show the highest proportions of CF$_3$H occurring at a temperature between 325° and 350° C. The "Other" reaction products (for 97.0 mol % of CF$_3$H) numbered four such products comprising 2.2 mol % of the reaction product stream.

TABLE 7

| | | RESULTS FOR EXAMPLE 7 | | | |
|---|---|---|---|---|---|
| Elapsed Time (hr) | T (°C.) | Effluent Stream Constituents (mol %) | | | |
| | | CH$_4$ | CF$_3$H | CF$_3$Cl | Other |
| 1 | 225 | 76.7 | 0.1 | 0.0 | 23.2 |
| 2 | 225 | 74.5 | 0.3 | 0.0 | 25.2 |
| 3 | 225 | 57.5 | 2.5 | 0.0 | 40.0 |
| 4 | 225 | 71.6 | 0.7 | 0.0 | 27.7 |
| 5 | 250 | 77.0 | 0.5 | 0.0 | 22.5 |
| 6 | 250 | 79.6 | 0.4 | 0.0 | 20.0 |
| 9 | 300 | 35.9 | 18.9 | 0.1 | 45.1 |
| 10 | 300 | 35.0 | 18.5 | 0.1 | 46.4 |
| 11 | 325 | 4.9 | 86.3 | 0.0 | 8.8 |
| 14 | 325 | 6.7 | 79.5 | 0.0 | 13.8 |
| 15 | 350 | 0.6 | 97.0 | 0.1 | 2.3 |
| 18 | 350 | 0.6 | 96.8 | 0.1 | 2.5 |

EXAMPLE 8

The same equipment and procedures were used as in Example 5, except that the initial catalyst charge was 9.6 g (15 cm$^3$) of COCl$_2$/Al$_2$O$_3$ (2% Co). Results are shown in Table 8.

The results show the highest proportion of CF$_3$H occurring at 375° C. Eight other reaction products were present in the reaction product stream exiting the reactor (after removal of HCl, Cl$_2$ and HF), the largest of which was 11.5 to 12 mol % of CH$_2$Cl$_2$, the other reaction products being present at 3.1 mol % and less.

TABLE 8

| | | RESULTS FOR EXAMPLE 8 | | | |
|---|---|---|---|---|---|
| Elapsed Time (hr) | T (°C.) | Effluent Stream Constituents (mol %) | | | |
| | | CH$_4$ | CF$_3$H | CF$_3$Cl | Other |
| 1 | 200 | 73.1 | 2.5 | 0.0 | 24.4 |
| 6 | 250 | 72.3 | 0.3 | 0.0 | 27.4 |
| 9 | 300 | 60.1 | 1.3 | 0.0 | 38.6 |
| 12 | 325 | 39.8 | 8.0 | 0.4 | 51.8 |
| 13 | 325 | 40.5 | 7.8 | 0.4 | 51.3 |
| 14 | 350 | 17.6 | 31.6 | 0.2 | 50.6 |
| 15 | 350 | 18.3 | 31.1 | 0.2 | 50.4 |

TABLE 8-continued
RESULTS FOR EXAMPLE 8

| Elapsed Time (hr) | T (°C.) | Effluent Stream Constituents (mol %) | | | |
|---|---|---|---|---|---|
| | | CH$_4$ | CF$_3$H | CF$_3$Cl | Other |
| 16 | 375 | 4.7 | 71.8 | 1.0 | 22.5 |
| 17 | 375 | 5.1 | 70.3 | 1.0 | 23.6 |

What is claimed is:

1. Process consisting essentially of contacting and reacting CH$_4$ simultaneously with Cl$_2$ and HF as the essential compounds present during said reacting, all in the gaseous state, under such conditions of temperature between 200° C. and 700° C., presence of thermally stable chlorofluorination catalyst which is an oxide or halide of metal selected from the group consisting of Groups IIA, IIB, IIIB, VIA, and VIIIA of the Periodic Table, catalyst contact time of less than 30 sec., and ratio of reactants wherein the molar ratio of CH$_4$/Cl$_2$/HF is at least 1/3/3 and optionally recycling unreacted reactant and byproduct to the contacting and reacting step to obtain as a result thereof at least 50 mol % of at least one reaction product selected from the group consisting of CF$_3$H, CF$_4$ and the combination thereof.

2. The process of claim 1 wherein said temperature is 250° C. to 600° C.

3. The process of claim 2 wherein the CF$_3$H obtained is at least 70 mol %.

4. The process of claim 3 wherein said temperature is 300° C. to 425° C.

5. The process of claim 2 wherein the molar rates of CH$_4$/Cl$_2$/HF is at least 1/4/4 and the CF$_4$ obtained is at least 50 mol %.

6. The process of claim 5 wherein said temperature is 450° C. to 550° C.

7. The process of claim 1 wherein said catalyst contact time is from 0.1 to 10 seconds.

8. The process of claim 1 wherein said catalyst is Cr$_2$O$_3$.

9. The process of claim 8 wherein the molar ratio of CH$_4$/Cl$_2$/HF is at least 1/4/6.

10. The process of claim 2 wherein the CF$_3$H obtained is at least 90 mol %.

11. Process consisting essentially of contacting and reacting CH$_4$ simultaneously with Cl$_2$ and HF as the essential compounds present in the process, all in the gaseous state, under such conditions of temperature within the range of about 250° C. to 600° C., presence of thermally stable chlorofluorination catalyst which is an oxide or halide of metal selected from the group consisting of Groups IIA, IIB, IIIB, VIA, and VIIIA of the Periodic Table, catalyst contact time of 0.1 to 10 seconds, and ratio of reactants wherein the molar ratio of CH$_4$/Cl$_2$/HF is at least 1/3/3 to obtain as a result thereof at least 50 mol % of at least one reaction product selected from the group consisting of CF$_3$H, CF$_4$ and the combination thereof.

12. The process of claim 10 wherein the CF$_3$H obtained is at least 70 mol % and said temperature is 300° C. to 425° C.

13. The process of claim 1 wherein the CF$_4$ obtained is at least 50 mol %, said temperature is 450° C. to 550° C., and the molar ratio of CH$_4$/Cl$_2$/HF is at least 1/4/4.

14. The process of claim 1 wherein the amount of chlorocarbon obtained is less than about 10 mol %.

15. The process of claim 1 wherein the CF$_3$H obtained is at least about 90 mol %.

16. The process of claim 15 wherein the amount of chlorocarbon obtained is less than about 5 mol %.

17. Process consisting of contacting and reacting CH$_4$ simultaneously with Cl$_2$ and HF as the essential compounds present during said reacting, all in the gaseous state, under such conditions of temperature between 200° C. and 700° C., presence of thermally stable chlorofluorination catalyst which is an oxide or halide of metal selected from the group consisting of Groups IIA, IIB, IIIB, VIA, and VIIIA of the Periodic Table, catalyst contact time of less than 30 sec., and ratio of reactants wherein the molar ratio of CH$_4$/Cl$_2$/HF is at least 1/3/3 and recycling unreacted reactant and byproduct to the contacting and reacting step to obtain as a result thereof at least 50 mol % of at least one reaction product selected from the group consisting of CF$_3$H, CF$_4$ and the combination thereof.

18. Process consisting of contacting and reacting CH$_4$ simultaneously with Cl$_2$ and HF as the essential compounds present during said reacting, all in the gaseous state, under such conditions of temperature between 200° C. and 700° C., presence of thermally stable chlorofluorination catalyst which is an oxide or halide of metal selected from the group consisting of Groups IIA, IIB, IIIB, VIA, and VIIIA of the Periodic Table, catalyst contact time of less than 30 sec., and ratio of reactants wherein the molar ratio of CH$_4$/Cl$_2$/HF is at least 1/3/3 to obtain as a result thereof at least 50 mol % of at least one reaction product selected from the group consisting of CF$_3$H, CF$_4$ and the combination thereof.

* * * * *